United States Patent [19]

Walsh

[11] Patent Number: 5,358,651
[45] Date of Patent: Oct. 25, 1994

[54] COMPOSITIONS, CONCENTRATES, LUBRICANT COMPOSITIONS, FUEL COMPOSITION AND METHODS FOR IMPROVING FUEL ECONOMY OF INTERNAL COMBUSTION ENGINES

[75] Inventor: Reed H. Walsh, Mentor, Ohio

[73] Assignee: The Lubrizol Corporation, Wickliffe, Ohio

[21] Appl. No.: 626,812

[22] Filed: Dec. 13, 1990

Related U.S. Application Data

[60] Division of Ser. No. 471,657, Jan. 23, 1990, Pat. No. 4,997,594, which is a continuation of Ser. No. 283,691, Dec. 13, 1988, abandoned, which is a division of Ser. No. 791,260, Oct. 25, 1985, abandoned.

[51] Int. Cl.$^5$ ............... C10M 133/56; C10M 133/16
[52] U.S. Cl. .................................. 252/51.5 A; 548/547
[58] Field of Search .................... 252/51.5 A; 548/547

[56] References Cited

U.S. PATENT DOCUMENTS

| | | | |
|---|---|---|---|
| 2,628,942 | 2/1953 | Morris et al. | 252/49.7 |
| 3,018,291 | 1/1962 | Anderson et al. | 260/326.5 |
| 3,068,082 | 12/1962 | Paris et al. | 44/63 |
| 3,401,118 | 9/1968 | Benoit, Jr. et al. | 44/63 |
| 3,451,931 | 6/1969 | Kahn et al. | 252/32.7 |
| 3,649,229 | 3/1972 | Otto | 44/73 |
| 3,723,460 | 3/1973 | Brannen et al. | 252/46.4 |
| 3,910,951 | 10/1975 | Fuerst et al. | 548/545 |
| 4,094,802 | 6/1978 | Soula et al. | 252/51.5 A |
| 4,153,564 | 5/1979 | Chibnik | 548/545 |
| 4,159,956 | 7/1979 | de Vries | 252/51.5 A |
| 4,234,435 | 11/1980 | Meinhardt et al. | 252/51.5 A |
| 4,240,803 | 12/1980 | Andreas, Jr. | 252/51.5 A |
| 4,292,186 | 9/1981 | Chibnik et al. | 252/49.7 |
| 4,482,464 | 11/1984 | Karol et al. | 252/51.5 A |
| 4,495,088 | 1/1985 | Liston | 252/51.5 A |
| 4,521,318 | 6/1985 | Karol | 252/51.5 A |
| 4,699,724 | 10/1987 | Nalesnik et al. | 252/51.5 A |
| 4,705,642 | 11/1987 | Sung et al. | 252/51.5 A |
| 4,714,561 | 12/1987 | Hoke | 252/51.5 A |

FOREIGN PATENT DOCUMENTS

| | | |
|---|---|---|
| 20037 | 5/1980 | European Pat. Off. |
| 0074199 | 3/1983 | European Pat. Off. |
| 1054280 | 1/1967 | United Kingdom |
| 1575467 | 9/1980 | United Kingdom |

OTHER PUBLICATIONS

*Chemistry of Organic Compounds*, Noller, 2nd. Ed., WB. Saunders Co., N.Y. 1957, pp. 198,199,202,203,209,210 (No month available).
Methodin der Organischen Chemie (Houben–Weyl), Band VIII, 657 (1952) month unavailable.
Methoden der Organischen Chemie (Houben–Weyl), Band XIII/1, 449 (1970) month unavailable.
Methoden der Organischen Chemie (Houben–Weyl), Band XVI/2–Index of Classes of Compounds, Part b, pp. 114–116 (1987) month unavailable.

*Primary Examiner*—Margaret B. Medley
*Attorney, Agent, or Firm*—Joseph P. Fischer; Frederick D. Hunter, Sr.; James L. Cordek

[57] ABSTRACT

Succinimide derivatives represented by the formula:

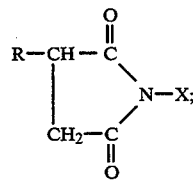

wherein X is selected from the group consisting of M,

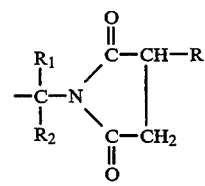

(I)

(Abstract continued on next page.)

-continued

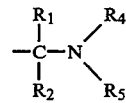
(III)

-continued

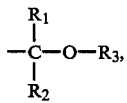
(II)

and wherein R is a hydrocarbon-based group containing from about 8 up to about 35 carbon atoms, $R_1$ and $R_2$ are each independently hydrogen or an alkyl group containing up to 8 carbon atoms; $R_4$ is a hydrocarbon-based group containing up to about 28 carbon atoms; $R_4$ and $R_5$ are each independently hydrogen or a hydrocarbon-based group containing up to about 25 carbon atoms; and M is a metal cation.

12 Claims, No Drawings

COMPOSITIONS, CONCENTRATES, LUBRICANT COMPOSITIONS, FUEL COMPOSITION AND METHODS FOR IMPROVING FUEL ECONOMY OF INTERNAL COMBUSTION ENGINES

This is a divisional of copending applications(s) Ser. No. 07/471.657 filed on Jan. 23, 1990, now U.S. Pat. No. 4,997,594 dated Mar. 5, 1991, which is a continuation of Ser. No. 07/283,691 filed on Dec. 13, 1988, now abandoned, which is a divisional of Ser. No. 06/791,260, filed Oct. 25, 1985, now abandoned.

BACKGROUND OF THE INVENTION

This invention relates to compositions useful as lubricant and fuel additives and methods for improving the operation of internal combustion engines, specifically by reducing the amount of fuel consumed by such engines. More particularly, the invention comprises lubricating compositions which may be used in such engines to decrease fuel consumption, and a method of using such lubricating compositions to accomplish this purpose. This invention also relates to a method for preparing these compositions. Additionally, this invention relates to concentrates and fuel composition comprising these compositions.

Efforts to reduce the amount of fuel consumed by internal combustion engines such as automobile engines have increased in recent years as a result of the petroleum shortage, the increased cost of petroleum products, and the desire for conservation of natural resources such as petroleum. It is recognized that a situation under which fuel consumption is minimized is desirable, both because of the conservation factor and because such a situation is economical for the user of the engine.

Many of the proposed solutions to the fuel conservation problem have been mechanical as, for example, adjusting the engine for a leaner burn or simply building smaller cars and smaller engines. Other efforts have related to developing lubricants that reduce the overall friction of the engine thereby reducing energy requirements. Some synthetic lubricants have been developed and compounded for use in the automobile engine to reduce fuel consumption. A considerable amount of effort has been expended toward developing additives for use in mineral lubricating oils and greases to reduce the friction properties of the oils and greases.

The following publications are exemplary of art in this area:

U.S. Pat. No. 3,796,663 describes N-hydroxy hydrocarbyl-substituted cyclic imides of $C_4$-$C_5$ dicarboxylic acids, e.g., hydrocarbyl-substituted succinyl and glutaric hydroximides, as rust inhibition, wear reduction and frictional control additives for lubricating oils.

U.S. Pat. No. 4,104,182 describes a lubricating oil composition comprising a hydrocarbyl oil of lubricating viscosity, a metals-containing additive characterized by promoting the formation of hard deposits in an internal combustion engine, and a hydrocarbon-substituted succinimide represented by the formula:

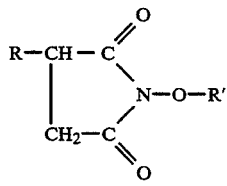

in which R is an aliphatic hydrocarbon radical having from about 1 to 50 carbon atoms and R' is a hydrocarbon radical having from 3 to 20 carbon atoms, and a method for lubricating an internal combustion engine.

U.S. Pat. No. 4,325,827 describes a fuel efficient motor oil which contains a friction-reducing amount of an N-hydroxymethyl $C_{12-36}$ aliphatic hydrocarbyl succinimide. This patent also describes these additives as being used in liquid hydrocarobn engine fuel.

European Patent Application 20,037 describes oil soluble $C_{12-36}$ aliphatic hydrocarbyl succinimide or succinamide which provides a friction reducing effect where it is incorporated in a lubricating oil.

SUMMARY OF THE INVENTION

In it broadest sense, the present invention provides a composition comprising one or more substituted succinimide derivatives represented by the formula:

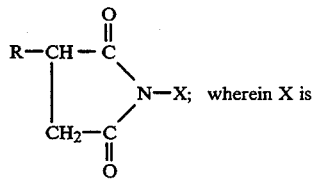

selected from the group consisting of M,

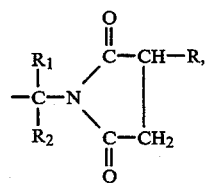

(I)

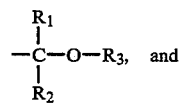

(II)

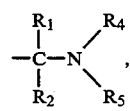

(III)

wherein R is a hydrocarbon-based group containing from about 8 up to about 35 carbon atoms, $R_1$ and $R_2$ are each independently hydrogen or an alkyl group containing up to 8 carbon atoms; $R_3$ is a hydrocarbon-based group containing up to about 28 carbon atoms; $R_4$ and $R_5$ are each independently hydrogen or a hydrocarbon-based group containing up to about 25 carbon atoms; and M is a metal cation; and the use of such compositions in lubricating oils and normally liquid fuels. Lubricating oils containing the compositions of the invention are effective in reducing the amount of fuel consumed by internal combustion engines. The invention also relates to a method of reducing the amount of fuel consumed by an internal combustion engine. In addition, lubricating oils containing the compositions of this invention are effective deposit softeners in internal combustion engines. This invention also relates to methods for preparing these substituted succinimide derivatives which are discussed hereinafter.

DETAILED DESCRIPTION OF THE INVENTION

Generally, in the substituted succinimide derivatives of this invention, R is a hydrocarbon-based group containing from about 8 up to about 35 carbon atoms.

As used herein, the term "hydrocarbon-based group" denotes a radical having a carbon atom directly attached to the remainder of the molecule and having predominantly hydrocarbon character within the context of this invention. Such groups include the following:

(1) Hydrocarbon groups; that is, aliphatic (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such groups are known to those skilled in the art.

(2) Substituted hydrocarbon groups; that is, radicals containing nonhydrocarbon substituents which, in the context of this invention, do not alter the predominantly hydrocarbon character of the radical. Those skilled in the art will be aware of suitable substituents; examples are halo, alkoxy, hydroxy, alkylthio, carbalkoxy, nitro and carboxyl.

(3) Hetero groups; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based group.

Terms such as "alkyl hydrocarbon-based group," "aliphatic hydrocarbon-based group," "aryl hydrocarbon-based group" and the like have meanings analogous to the above with respect to alkyl, aliphatic and aryl groups and the like.

Preferably, the hydrocarbon-based groups in the compositions of this invention are free from acetylenic unsaturation.

As used in the present specification and claims, the term "lower," when used in conjunction with terminology designating a chemical group such as alkyl, alkenyl, alkylene and the like, is intended to describe such groups having a total carbon atom content of up to and including 7. For example, "lower alkyl" includes all straight and branched chain alkyl groups of up to and including 7 carbon atoms.

Typically the substituent groups are aliphatic hydrocarbon-based groups containing from about 8 up to about 35 carbon atoms, preferably from about 10 up to about 30 carbon atoms and more preferably from about 12 up to about 28 carbon atoms. The R group may be a branched chain or straight chain configuration; however, it is preferred that at least 8 carbon atoms are in a straight chain configuration and, more preferably, is substantially straight chain configuration. Furthermore, the R group is preferably alkyl or alkenyl.

The term "substantially straight-chain" means that the group contains no more than about 2 methyl groups.

Generally $R_1$ and $R_2$ are each independently hydrogen or an alkyl group containing up to 8 carbon atoms, preferably up to about 3 carbon atoms. Usually, at least one of $R_1$ and $R_2$ is hydrogen and, preferably, both $R_1$ and $R_2$ are hydrogen.

Typically, $R_3$ is a hydrocarbon-based group containing up to about 24 carbon atoms. Usually, $R_3$ is an aliphatic hydrocarbon-based group containing from 4 up to about 28 carbon atoms, preferably, from about 8 up to about 28 carbon atoms. The $R_3$ group may be a branch chain or straight. chain configuration; however, it is preferred that at least 8 carbon atoms are in a straight chain configuration and, more preferably, is substantially straight chain configuration. Furthermore, $R_3$ is preferably alkyl or alkenyl.

Generally, $R_4$ and $R_5$ are each independently hydrogen or a hydrocarbon-based group containing up to about 25 carbon atoms. Usually, $R_4$ and $R_5$ are both hydro-carbon-based groups. Typically, $R_4$ and $R_5$ are each independently hydrogen or a hydrocarbon-based group containing up to about 18 carbon atoms. $R_4$ and $R_5$ may be branched or straight chain configurations; however, it is preferred that at least 8 carbon atoms are in a straight chain configuration and, more preferably, is substantially straight chain configuration. Furthermore, $R_4$ and $R_5$ are preferably alkyl or alkenyl. In addition, $R_4$ and $R_5$, when taken together with the nitrogen to which each is attached, form a heterocyclic ring.

As used herein, M is a metal cation. The metal may be chosen from Group Ia, Ib, IIa or IIb of the Periodic Table (Chemical Abstracts Service Version), although metals from Groups IVa, IVb, Va, Vb, VIa, VIb, VIIa, VIIb and VIII can also be used. Preferably, M is selected from the group consisting of lithium, sodium, potassium, calcium, barium and zinc. The substituted succinimide derivatives of this invention in which X is M may be metal complexes, metal salts or mixtures thereof. The metal salts formed can be "acidic," "neutral" or "basic" salts. An "acidic" salt is one in which the equivalents of succinimide exceed the stoichiometric amounts required to neutralize the number of equivalents of metal. A "neutral" salt is one wherein the metal and succinimide are present in stoichiometrically equivalent amounts. A "basic" or "overbased" salt (sometimes referred to as "superbased" or "hyperbased" salts) is one wherein the metal is present in a stoichiometric excess relative to the number of stoichiometric equivalents of substituted succinimide from which it is produced.

The substituted succinimide metal derivatives of the instant invention include coordination compounds. Such compounds being a complex of the substituted succinimide and the metal cation. Coordination compounds are well known to those of ordinary skill and are described in detail in "Advanced Inorganic Chemistry—A Comprehensive Text" by F. A. Cotton and G. Wilkenson (1967), pages 124–190, which is hereby incorporated by reference for its relevant disclosures pertaining to coordination compounds and their preparation.

Preferred are the substituted succinimide metal derivatives wherein there is about 1 equivalent of metal for each equivalent of succinimide. For the purposes of this invention, an equivalent of succinimide is equal to one mole of succinimide. Also, the purposes of this invention, one equivalent of a metal is equal to the molecular weight of that metal divided by the valence of the metal ion. Sodium has an equivalent weight of 23 (23 divided by 1); calcium has an equivalent weight of 20 (40 divided by 2).

The substituted succinimide derivatives of the instant invention in which X is M can be prepared by reacting one or more substituted succinimides represented by the formula

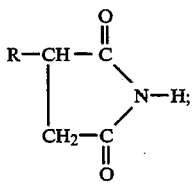

wherein R is defined hereinabove, with at least one reactive metal, reactive metal derivative or mixtures thereof.

The substituted succinimide useful for preparing the substituted succinimide derivatives of the present invention are typically prepared by reacting a substituted succinic acid or derivative thereof, with ammonia to form the imide. The substituted succinic acids and their derivatives (e.g., anhydrides, acid halides, esters) of this type may be conveniently prepared by the reaction of maleic or fumaric acid or a derivative thereof, preferably maleic anhydride, with one or more olefins containing from about 8 to about 35 carbon atoms.

The substituted succinimides and the substituted succinic acid or derivatives thereof useful for the purposes of this invention are well known to those of ordinary skill in the art. Some of these are described in U.S. Pat. Nos. 4,3251,827; 4,324,872; 4,158,664; 4,000,163; 3,819,660; 3,796,663; 3,412,111; 3,382,172; and 2,411,215. These patents are hereby incorporated by reference for their teachings of substituted succinimides and substituted succinic acids or derivatives thereof and methods for preparing such compositions.

The substituted succinimide derivatives of the instant invention in which X is M can be made by conventional techniques well known to those of ordinary skill in the art. Preferably they are made from a reactive metal, mixture of reactive metals, or a reactive metal derivative such as a metal salt or mixture of metal salts where the metal is chosen from Group Ia, Ib, IIa or IIb of the Periodic Table (Chemical Abstracts Service version) although metals from Groups IVa, IVb, Va, Vb, VIa, VIb, VIIb and VIII can also be used. The anion can be inorganic such as halide, sulfide, oxide, carbonate, hydroxide, nitrate, sulfate, thiosulfate, phosphite, phosphate, etc., or organic such as lower alkanoic, sulfonate, alcoholate, etc. The salts formed from these metals and the substituted succinimides can be "acidic," "neutral" or "basic" salts. "Acidic", "neutral" and "basic" salts and methods for their preparation are well known to those of ordinary skill in the art and further discussion is, therefore, unnecessary. The production of overbased salts are described in detail in "Lubricant Additives" by M. W. Ranney, pages 67–77, which is hereby incorporated by reference for its relevant disclosures pertaining to methods for preparing overbased salts. Preferred are metal salts derived from metals selected from the group consisting of lithium, sodium, potassium, magnesium, calcium, barium, zinc and mixtures thereof. Also preferred is a ratio of equivalents of substituted succinimide to equivalents of reactive metal or reactive metal derivatives of about 1:1.

The substituted succinimide derivatives in which X is M can be coordination compounds of such metals or mixtures of one or more salts and one or more coordination compounds.

The substituted succinimide derivatives of the instant invention in which X is represented by the formula:

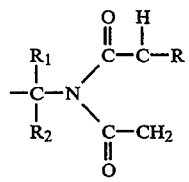 (I)

wherein R, $R_1$ and $R_2$ are defined hereinabove can be prepared by reacting in the presence of a catalytic amount of base:

A) one or more substituted succinimides represented by the formula:

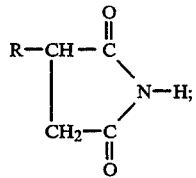

wherein R is a hydrocarbon-based group containing from about 8 up to about 35 carbon atoms; with B) one or more carbonyl compounds represented by the formula:

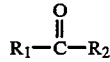

wherein $R_1$ and $R_2$ are each independently hydrogen or an alkyl radical containing up to 8 carbon atoms.

The substituted succinimides (A) are described hereinabove.

The base catalyst may be inorganic oxides and salts such as sodium hydroxide, calcium oxide, calcium hydroxide, sodium sulfide, sodium carbonate and sodium bicarbonate Other base catalysts include sodium acetate, sodium propronate and amines. The amines include primary, secondary and tertiary hydrocarbyl amines wherein the hydrocarbyl radicals are alkyl, aryl, aralkyl, alkaryl or the like and contain about 1–20 carbon atoms. Suitable amines include aniline, benzylamine, dibenzylamine, dodecylamine, naphthylamine, tallow amines, N-ethyldipropylamine, N-phenylbenzylamine, N,N-diethylbutylamine, m-toluidine and 2,3-xylidine. Also useful are heterocyclic amines such as pyrrolidine, N-methylpyrrolidine, piperidine, pyridine and quinoline.

The preferred basic catalyst is sodium hydroxide.

The amount of catalytic material used is generally about 0.05 to 2.0 percent of the weight of the reaction mixtures. In the case of the preferred sodium hydroxide catalyst, about 0.005–0.5 mole per mole of substituted succinimide is preferred, and about 0.001–0.1 mole is especially desirable.

The carbonyl compounds of this invention are the aldehydes and ketones corresponding to the formula:

wherein $R_1$ and $R_2$ are as previously defined.

Examples of aldehydes which are within the scope of this invention include formaldehyde, acetalaldehyde, propionaldehyde, n-butyraldehyde, isobutyraldehyde, n-valeraldehyde, isovaleraldehyde, alpha-methylbutyraldehyde, n-caprioicaldehyde, isocaprioicaldehyde, 2-ethylbutyraldehyde, methyl-n-propylacetaldehyde, ethylisobutyraldehyde, n-heptaldehyde, ethylisopropylacetaldehyde, 3,3-dimethylpentanal, 5-methylhexanal, caprylaldehyde, 2-ethylhexanal-1, capraldehyde, di-n-propylacetaldehyde, and the like. Mixtures of two or more such aldehydes can be used.

The preferred aldehydes are formaldehyde or functional equivalents thereof. Such functional equivalents are materials (e.g., solutions, polymers, hydrates, etc.) which react as aldehydes under the conditions of the reaction and include paraformaldehyde, formalin and methylal. Examples of ketones which are in the scope of this invention include acetone, methylethyl ketone, 2-pentanone, 2-methyl-3-butanone, 3-hexanone, 4-methyl-2-pentanone, cyclobutylmethylketone, 1-methoxy-2-pentanone, 2-heptanone, 4-heptanone, 2,2-dimethyl-3-pentanone, 2,4-dimethyl-3-pentanone, and the like. Mixtures of two or more such ketones can be used. Also, mixtures of one or more aldehydes and one or more ketones can be used. Preferably, the carbonyl compound is an aldehyde and, more preferably, formaldehyde or functional equivalent thereof.

Usually, there is at least about one mole of carbonyl compound for every two moles of succinimide, preferably, about one mole of carbonyl compound for every two moles of succinimide.

The substituted succinimide derivatives of the instant invention in which X is represented by the formula:

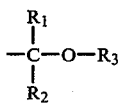 (II)

wherein $R_1$, $R_2$ and $R_3$ are defined hereinabove can be prepared by reacting in the presence of a catalytic amount of base:

A) one or more substituted succinimides represented by the formula:

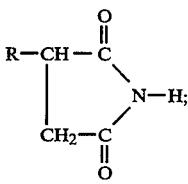

wherein R is a hydrocarbon-based group containing from about 8 up to about 35 carbon atoms;

B) one or more carbonyl compounds represented by the formula:

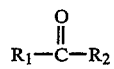

wherein $R_1$ and $R_2$ are each independently hydrogen or an alkyl radical containing up to 8 carbon atoms, and C) at least one alcohol represented by the formula:

$$R_3\text{—OH}$$

wherein $R_3$ is a hydrocarbon-based group containing up to about 28 carbon atoms.

The substituted succinimides, the catalytic base and carbonyl compounds are discussed hereinabove.

The alcohols are those represented by the formula:

wherein $R_3$ is described hereinabove.

Preferably the alcohols useful for the purposes of this invention are monohydric alcohols and can comprise, for example, primary and secondary aliphatic alcohols. The preferred monohydric alcohols, however, are primary aliphatic alcohols, especially aliphatic hydrocarbon alcohols such as alkenols and alkanols of from about 4 to about 28 carbon atoms, and preferably from about 8 to about 22 carbon atoms. More preferably, $R_3$ is derived from a monohydric alcohol containing up to about 14 carbon atoms. Accordingly, examples of the preferred monohydric alcohols from which the R group is derived include 1-octanol, 1-decanol, 1-dodecanol, 1-tetradecanol, 1-hexadecanol, 1-octadecanol, oleyl alcohol, linoleyl alcohol, linolenyl alcohol, phytol, myricyl alcohol, lauryl alcohol, myristyl alcohol, cetyl alcohol, stearyl alcohol and behenyl alcohol.

Of course, commercial alcohols (mixtures) are contemplated herein, and these commercial alcohols may comprise minor amount of alcohols which, although not specified herein, do not detract from the major purposes of this invention. Higher synthetic monohydric alcohols of the type formed by the Oxo process (e.g., 2-ethylhexyl), the aldol condensation, or by organoaluminim-catalyzed oligomerization of alpha-olefins (especially ethylene), followed by oxidation, also are useful.

Examples of some preferred monohydric alcohols and alcohol mixtures suitable for forming the compositions of the invention include commercially available "Alfol" alcohols marketed by Continental Oil Corporation. Alfol 810 is a mixture containing alcohols consisting essentially of straight chain, primary alcohols having from 8 to 10 carbon atoms. The Alfol 20+ alcohols are mixtures of $C_{18}$–$C_{28}$ primary alcohols having mostly, on an alcohol basis, $C_{20}$ alcohols as determined by GLC (gas-liquid-chromatography). The Alfol 22+ alcohols are $C_{18}$–$C_{28}$ primary alcohols having mostly, on an alcohol basis, $C_{22}$ alcohols. These Alfol alcohols can contain a fairly large percentage (up to 40 percent by weight) of paraffinic compounds which can be removed before the esterification reaction if desired.

Another example of a commercially available alcohol mixture is Adol 60 which comprises about 75 percent by weight of a straight chain $C_{22}$ primary alcohol, about 15 percent of a $C_{20}$ primary alcohol and about 8 percent of $C_{18}$ and $C_{24}$ alcohols. Adol 60 is marketed by Ashland Chemical.

A variety of mixtures of monohydric fatty alcohols derived from naturally occurring triglycerides and ranging in chain length of from $C_8$ to $C_{18}$ are available from Procter & Gamble Company. These mixtures contain various amounts of fatty alcohols containing mainly 12, 14, 16, or 18 carbon atoms. For example, CO-1214 is a fatty alcohol mixture containing 0.5 percent of $C_{10}$ alcohol, 66.0 percent of $C_{12}$ alcohol, 26.0 percent of $C_{14}$ alcohol and 6.5 percent of $C_{16}$ alcohol.

Another group of commercially available mixtures include the "Neodol" products available from Shell Chemical Co. For example, Neodol 23 is a mixture of $C_{12}$ and $C_{13}$ alcohols; Neodol 25 is a mixture of $C_{12}$ and $C_{15}$ alcohols; and Neodol 45 is a mixture of $C_{14}$ and $C_{15}$ alcohols.

Fatty vicinal diols also are useful and these include those available from Viking Chemical Company under the general trade designation Vikinol 12 and Vikinol 16. The former is derived from a 12 carbon straight chain alpha-olefin fraction of and the latter is derived from a 16 carbon fraction.

Examples of preferred branched chain monohydric alcohols suitable for use in the present invention include, for example, commercial tridecyl alcohol corresponding in large part substantially to the formula:

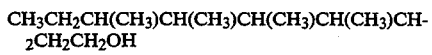

prepared by the Oxo process and which is available from Exxon Corporation, hexadecyl alcohol prepared by the Oxo process, 12-methylpentadecyl alcohol, 6-methyldecyl alcohol, 8-ethyltetradecyl alcohol, 5,6-dipropyldecyl alcohol as well as mixtures of these alcohols. Branched chain alcohols of from 12 to 14 carbon atoms with one or more methyl branches are the more preferred.

Typically, the molar ratio of succinimide (A):carbonyl compound (B):alcohol (C) is 1:1:1, although an excess of carbonyl compound is preferred in order to drive the reaction to completion. Preferably, the molar ratio of (A):(B):(C) is 1:1–1.3:1 and more preferably 1:1–1.1:1.

The substituted succinimide derivatives of the instant invention in which X is represented by the formula:

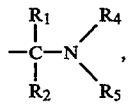

wherein $R_1$, $R_2$, $R_4$ and $R_5$ are defined hereinabove, can be prepared by reacting in the presence of a catalytic amount of base:

A) one or more substituted succinimides represented by the formula:

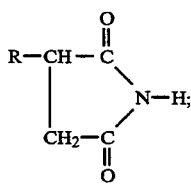

wherein R is a hydrocarbon-based group containing from about 8 up to about 35 carbon atoms;

B) one or more carbonyl compounds represented the formula:

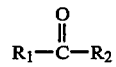

wherein $R_1$ and $R_2$ are each independently hydrogen or an alkyl radical containing up to 8 carbon atoms; and C) one or more amines represented by the formula:

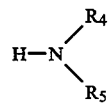

wherein $R_4$ and $R_5$ are each independently hydrogen or a hydrocarbon-based group containing up to about 25 carbon atoms.

The substituted succinimides, the catalytic base and carbonyl compounds are discussed hereinabove.

The amines suitable for use in this invention are those represented by the formula:

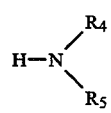

wherein $R_4$ and $R_5$ are defined hereinabove.

The amines can be monoamines or polyamines.

Preferably, $R_4$ and R5, when hydrocarbon-based groups, are substantially saturated. This means that each $R_4$ and $R_5$ contains no more than 1 carbon-to-carbon unsaturated bond for about every 10 carbon-to-carbon single bonds present in the group. Usually they contain no more than 1 carbon-to-carbon nonaromatic unsaturated bond. Typically, however, the amines of this invention, both mono- and polyamines, contain only carbon, hydrogen, nitrogen and, in certain instances (as described below) oxygen in the form of ether linkages.

Usually, $R_4$ and $R_5$ groups which are hydrocarbon groups contain about 4 to about 25 carbon atoms. Preferably, these are alkyl groups of about 4 to about 18 carbon atoms or aromatic groups containing 6 to about 18 carbon atoms. Specific examples of such amines include n-butylamine, isobutylamine, di(n-butyl)amine, 2-ethylhexylamine, cocoamine, stearylamine, laurylamine, and oleylamine. Details as to these and other alkyl amines are found in Kirk Othmer Encyclopedia of Technology, Third Edition, Volume II, John Wiley and Sons, New York, N.Y. (1978), pages 272–354, particularly those articles entitled "Lower Aliphatic Amines" and "Fatty Amines." The amine can also be an aromatic amine such as aniline, p-methylaniline, benzyl amine, the various tolyl amines, diphenylamine, dibenzylamine, etc. These are also described in Kirk Othmer cited above, particularly beginning at page 309.

The amines used in making the inventive compositions can also be polyamines. Such amines contain more than one amine group which can be all of one type (e.g., primary) or of various types. Among the polyamines are aliphatic and aromatic polyamines, such as 1,3-cyclohexyldiamine, various diamino toluenes, methylenedianiline, phenylenediamines and the like. A typical class of polyamines are the alkylene polyamines including those conforming for the most part to the formula:

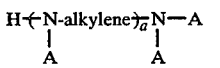

wherein a is an integer between 1 and about 10 (preferably between 2 and 8), each A is independently a hydrogen atom or a substantially hydrocarbyl group having up to about 20 carbon atoms with the proviso that two A groups can be taken together with N to form a ring of 5–6 annular members and up to 12 carbon atoms. Preferably A is a hydrogen atom or an aliphatic group of up to about 10 carbon atoms, and "alkylene" is a lower alkylene group of between 1 and about 10, preferably between 2 and about 6 carbon atoms. Commonly available and often used are the alkylene polyamines wherein each A is hydrogen and alkylene is an ethylene or propylene group. These encompass the well-known ethylene and propylene diamines and are exemplified specifically by ethylenediamine, triethylenetetraamine, tris(2-aminoethyl)amine, propylenediamine, trimethylenediamine, decamethylenediamine, di-heptamethylenetriamine and the like. Specific examples of these, particularly the ethylene polyamines are described in detail in Kirk Othmer, Encyclopedia of Chemical Technology, Third Edition, Volume 7, John Wiley and Sons, New York, N.Y. (1979), page 580, and following under the heading "Diamines and Higher Amines, Aliphatic" which is hereby incorporated by reference for its disclosures in this regard.

Also useful as amines in making the inventive compositions are ether amines which are similar to the aforedescribed amines except they contain one or more ether groups. These ether amines can be monoamines of the formula:

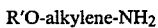

wherein R' is an alkyl group of up to about 20 carbon atoms and alkylene is an alkylene group containing up to 10 carbon atoms. In one preferred type, alkylene contains 3 carbon atoms and R' contains from about 4 to about 18 carbon atoms. Compounds of the type are available commercially.

Heterocyclic amines are also useful in making the compositions of this invention, provided they contain a primary or secondary amino group. The heterocyclic ring can also incorporate unsaturation and can be substituted with hydrocarbon radicals such as alkyl, alkenyl, aryl, alkaryl or aralkyl. In addition, the ring can also contain other hetero atoms such as oxygen, sulfur or other nitrogen atoms including those not having hydrogen atoms bonded to them. Generally, these rings have 3–10, preferably 5 or 6, ring members. Among such heterocycles are aziridines, azetidines, azolidines, pyridine, pyrroles, piperidines, imidazoles, indoles, piperazines, isoindoles, purines, morpholines, thiamorpholines, N-aminoalkyl morpholines, N-aminoalkyl thiamorpholines, azepines and tetrahydro-, dihydro- and perhydro-derivatives of each of the above. Preferred heterocyclic amines are the saturated ones with 5- and 6- membered rings, especially the piperidines, piperazines and morpholines described above.

Typically, the molar ratio of succinimide (A):carbonyl compound (B):amine (C) is 1:1:1, although an excess of carbonyl compound is preferred in order to drive the reaction to completion. Preferably, the molar ratio of (A):(B):(C) is 1:1–1.3:1 and, more preferably, 1:1–1.1:1.

The reaction process for the preparation of the compositions of this invention involving the use of a carbonyl compound is usually carried out for a period long enough for the condensation to be substantially complete. The reaction is considered complete when all the water of reaction is formed (one mole of water for each mole of carbonyl compound).

For practical purposes, one of ordinary skill in the art could determine the extent of water formation by standard techniques such as distillation, separation, and the like. Preferably, the water of reaction is removed continuously as it is formed. For purposes of this invention, the reaction is considered complete when about 90% of the theoretical amount of water to be formed (one mole of water for each mole of carbonyl compound) has been removed by such standard techniques. The reaction period can be about 0.5 to 72 hours, but is usually 0.5 to 24 hours at a temperature of from about 140° C. up to just below the decomposition temperature of any component of the reaction mixture, usually from about 180° up to 260° C.

Should any of the ingredients have a boiling point below that of the desired reaction temperature, the reaction may be conveniently carried out at super atmospheric pressures.

The reactions of this invention may be carried out in the presence of a substantially inert liquid solvent/diluent medium. This solvent/diluent medium desirably serves to maintain contact of the reactants and facilitates control of the reaction temperature. Examples of suitable solvent/diluent media include aliphatic and aromatic hydrocarbons as benzene, toluene, naphtha, mineral oil, hexane; chlorinated hydrocarbons as dichlorobenzene, and heptylchloride; ethers as methyl n-amylether, n-butylether.

As used in the specification and the appended claims, the term "substantially inert" when used to refer to solvents/diluents, and the like, is intended to mean that the solvent/diluent, etc., is sufficiently inert to chemical or physical change under the conditions in which it is used so as not to materially interfere in an adverse manner with the preparation, storage, blending and/or functioning of the compositions, additive, compound, etc., of this invention in the context of its intended use. For example, small amounts of a solvent/diluent, etc., can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, thus, readily understood and appreciated by those of ordinary skill in the art.

As used in the specification and the appended claims, the term "solvent/diluent medium" is intended to include those solvent/diluent media in which independently each of the reactants are soluble or stably dispersible. The term "stably dispersible" as used in the specification and the appended claims is intended to mean a composition (e.g., a single compound, a mixture of two or more compounds, etc.) is capable of being dispersed in a given medium to an extent which allows it to function in its intended manner. Thus, for example, where a composition is prepared by a reaction in an oil, it is sufficient that the reactants be capable of being suspended in the oil in a manner sufficient to allow the reaction to occur and the formation of the composition Thus, the term "solvent/diluent medium" is understood and can be used in a conventional manner by those of ordinary skill in the art.

The compositions of this invention may be used as a lubricant additive. However, the compositions sometimes may be accompanied by the formation of by-products and/or excess solvent/diluent medium which may lessen its commercial appeal. Accordingly, these undesirable by-product and/or excess of undesired solvent/diluent medium can be separated from the compositions of this invention by techniques known in the art; e.g., filtration, evaporation (e.g., stripping), etc., to obtain a more desirable product. Alternatively, if the solvent/diluent medium is, for example, a lubricant base suitable for use in the lubricating compositions of this invention, the product can be left in the solvent/diluent medium and used to form the lubricating compositions as described below.

This invention is exemplified in the following examples. Of course, these examples are not intended as limiting this invention as modification of the examples by ordinary expedient will be readily apparent to those of ordinary skill in the art.

In all examples, unless otherwise stated, all parts are parts by weight and all percentages are derived from parts by weight.

EXAMPLES 1

5775 parts (25.33 moles) of a commercially available $C_{15\text{-}18}$ alpha-olefin fraction (having a carbon number distribution of 1% $C_{14}$, 29% $C_{15}$, 28% $C_{16}$, 27% $C_{17}$, 14% $C_{18}$, and 1% $C_{19}$) are passed through 12-inch column packed with activated alumina into a 12-liter flask containing 2485 parts (25.35 moles) maleic anhydride. The mixture is heated to 214° C. and maintained at that temperature for 7 hours with a nitrogen sparge (0.2 standard cubic feet per hour) and then cooled to room temperature. The mixture is then heated to 209°–212° C. and maintained at that temperature for 7 hours, then cooled to room temperature. 1500 parts of textile spirits are added and the mixture is stirred for one hour. The mixture is filtered with diatomaceous earth. The mixture is stripped under a vacuum of 0.7 mm Hg. at 168° C. then cooled to room temperature. The mixture is filtered with diatomaceous earth at room temperature. The filtrate is the desired product.

EXAMPLE 2

A reaction vessel containing 2528 parts (8 moles) of the $C_{15\text{-}18}$ substituted succinic anhydride of Example 1 is heated to 100° C. Gaseous ammonia, 252 parts (14.8 moles), is slowly bubbled under the surface over two hours during which the temperature of the reaction mixture is increased to 280° C. Water of reaction is removed continuously during the ammonia addition. The reaction mixture is stripped at 180° C. under a vacuum of 15 mm Hg. The residue is a $C_{15\text{-}18}$ substituted succinimide having an acid number to phenolphthalein of 80 and a percent nitrogen of 4.81.

EXAMPLE 3

A mixture of 1264 parts (4 moles) of the $C_{15\text{-}18}$ substituted succinic anhydride of Example 1, 240 parts (4 moles) urea and 200 parts xylene is heated to reflux and water of reaction is removed by azeotropic distillation. The volatiles are removed at 160° C. and 22 mm Hg. The reaction mixture is filtered through a filter aid material to yield the desired $C_{15\text{-}18}$ succinimide with an acid number to phenolphthalein of 69.5.

EXAMPLE 4

Charged to a reaction vessel are 198 parts (2.02 moles) of maleic anhydride and 500 parts (1.36 moles) of a commercial mixture of $C_{18\text{-}24}$ olefins available from Ethyl Corporation wherein these olefins are typically 10% $C_{18}$, 45% $C_{20}$, 25% $C_{22}$ and 15% $C_{24}$ and are comprised predominantly of substantially straight chain alpha, 1,1-disubstituted and 1,2-disubstituted olefins. This reaction mixture is heated to 200° C. and held at 200°–220° C. for 10 hours. Unreacted starting materials are removed by vacuum distillation to 5 mm Hg. at 200° C. The reaction mixture is filtered to yield the desired $C_{18\text{-}24}$ substituted succinic anhydride having an acid number of 290.

EXAMPLE 5

A reaction vessel containing 5424 parts (12 moles) of the $C_{18\text{-}24}$ substituted succinic anhydride of Example 4 is heated to 120° C. Gaseous ammonia, 267 parts (15.7 moles), is slowly bubbled below the surface over 6.75 hours during which the temperature of the reaction mixture is increased to 240° C. Water of reaction is removed continuously during the $NH_3$ addition. The reaction mixture is stripped to 190° C. The residue is the $C_{18\text{-}24}$ substituted succinimide having an acid number to phenolphthalein of 69 and a per cent nitrogen of 2.91.

EXAMPLE 6

A mixture of 948 parts (6 moles) Neodol 91, a commercially available $C_9$ to $C_{11}$ primary alcohol from Shell typically having an approximate weight distribution of 20% $C_9$, 40% $C_{10}$ and 40% $C_{11}$ alcohols, 1890 parts (6 mole) of the $C_{15\text{-}18}$ substituted succinimide of Example 2, 180 parts (6 moles) para-formaldehyde and 48 parts (0.6 moles) of a 50% aqueous sodium hydroxide solution is heated at 150°–160° C. for 8 hours while passing a stream of nitrogen through the mixture at 2 cubic feet per hour to remove water by distillation. Concentrated hydrochloric acid, 58.2 parts (0.6 moles), is added dropwise to neutralize the sodium hydroxide catalyst and the reaction mixture is stripped to 160° C. The reaction mixture is filtered through a filter aid material to yield the desired product having a 2.09% nitrogen content and an acid number to phenolphthalein of 33.

EXAMPLE 7

A reaction mixture is prepared by adding 40 parts (0.5 moles) of a 50% aqueous sodium hydroxide solution to a mixture of 2215 parts (5 moles) of the $C_{18\text{-}24}$ substituted succinimide of Example 5, 150 parts (5 moles) paraformaldehyde and 790 parts (5 moles) Neodol 91 described in Example 6. The reaction mixture is heated to 160° C. while passing a stream of nitrogen through the mixture to remove the water of reaction. The reaction mixture is filtered through a filter aid material to yield the desired product having a 2.03% nitrogen content and an acid number to phenolphthalein of 24.

EXAMPLE 8

A mixture of 1353 parts (3 moles) of the $C_{18\text{-}24}$ substituted succinimide of Example 5, 24 parts (0.3 moles) of a 50% aqueous sodium hydroxide solution, 90 parts (3.0 moles) of paraformaldehyde and 200 parts xylene is heated to 180° C. while passing nitrogen through the mixture at 2 cubic feet per hour and removing volatiles continously. The reaction mixture is stripped of xylene. The contents are filtered through a filter material to give the desired product.

EXAMPLE 9

A reaction mixture is prepared by the dropwise addition of 73 parts (1 mole) of diethylamine to 482 parts (1 mole) of the product of Example 8. The reaction mixture is stripped to 160° C. and then filtered through a filter aid material to yield the desired product having a 3.36% nitrogen content and an acid number to phenolphthalein of 59.

EXAMPLE 10

A mixture of 482 parts (1 mole) of the product of Example 8 and 390 parts (1 mole) of Armeen 2C, a commercially available dicocoamine from Armak Corporation having the formula $(C_{12}H_{25})_2NH$ is heated to 180° C. Nitrogen is passed through the mixture at 1 cubic foot per hour. The reaction mixture is filtered through a filter aid material to yield the desired product having a 3.22% nitrogen content and an acid number to phenolphthalein of 23.

EXAMPLE 11

A mixture of 482 parts (1 mole) of the product of Example 8 and 490 parts (1 mole) of Armeen 2HT, a dihydrogenated tallow amine from Armak Corporation, having the formula $(C_{18}H_{37})_2NH$ is heated to 150° C. Nitrogen is passed through the mixture at 1 cubic foot per hour. The reaction mixture is filtered through a filter aid material to yield the desired product having a 2.79% nitrogen content and an acid number to phenolphthalein of 16.

EXAMPLE 12

A reaction mixture is prepared by adding 24 parts (0.03 moles) of a 50% aqueous sodium hydroxide solution and 136 parts (0.3 moles) of the product of Example 8 to a mixture of 12.89 parts (0.1 moles) cyanuric acid and 70 parts xylene heated to 90° C. The reaction mixture is heated to reflux and held for one hour, then stripped to 190° C. The reaction mixture is filtered through a filter aid material to give the desired product having a 3.55% nitrogen content and an acid number to phenolphthalein of 49.

EXAMPLE 13

A mixture of 443 parts (1 mole) of the $C_{18-24}$ substituted succinimide of Example 5, 117 parts xylene, 30 parts (1 mole) paraformaldehyde and 8 parts (0.1 moles) of a 50% aqueous sodium hydroxide solution is heated to reflux and held for one hour. Diethanolamine, 105 parts (1 mole) is added over two hours. This reaction mixture is then heated at reflux and water is removed by azeotropic distillation. The reaction mixture is filtered through a filter aid material to yield the desired product containing 20% xylene and having a 4.62% nitrogen content and an acid number to phenolphthalein of 31.

EXAMPLE 14

A mixture of 1329 parts (3 moles) of the $C_{18-24}$ substituted succinimide of Example 5, 522 parts (3 moles) morpholine, 90 parts (3 moles) paraformaldehyde and 24 parts (0.3 moles) of a 50% aqueous sodium hydroxide solution is heated at 110°–140° C. for 5 hours while removing water. This reaction mixture is cooled to 90° C. and then filtered through a filter aid material to give the desired product having a 5.82% nitrogen content.

EXAMPLE 15

A mixture of 902 parts (2 moles) of the $C_{18-24}$ substituted succinimide of Example 5, 100 parts xylene, 8 parts (0.1 moles) of a 50% aqueous sodium hydroxide solution and 33 parts (1.1 moles) paraformaldehyde is heated under a nitrogen blanket to 165° C. and water is removed by azeotropic distillation. The remaining volatiles are removed by vacuum distillation. The reaction mixture is filtered through a filter aid material to yield the desired product having a 2.83% nitrogen content and an acid number to phenolphthalein of 52.

EXAMPLE 16

A mixture of 886 parts (2 moles) of the $C_{18-24}$ substituted succinimide of Example 5, 300 parts xylene and 112 parts (2 moles) powdered potassium hydroxide are heated to reflux and water is removed by azeotropic distillation. The reaction mixture is then stripped to 150° C. at 10 mm Hg. vacuum. The residue is the desired oil containing product having a 2.23% nitrogen content, 5.76% potassium content and a base number to bromophenol blue of 75.

EXAMPLE 17

A mixture of 222 parts (0.5 moles) of the $C_{18-24}$ substituted succinimide of Example 5, 100 parts xylene, 20 parts sodium hydroxide (0.5 moles) and 84 parts diluent oil are heated to reflux and water is removed by azeotropic distillation. The xylene is stripped out and the reaction mixture is filtered through a filter aid material to yield the desired product having a 3.73% sodium content and a base number to bromophenol blue of 75.

EXAMPLE 18

A reactor is charged with 304 parts (4 moles) of 2-methoxyethanol and is heated to 120° C. Magenesium metal is charged in 5 increments with each increment being reacted before charging the next increment. A total of 24 parts (1 mole) of magnesium is added in this manner. At 140° C., a mixture of 886 parts (2 moles) of the $C_{18-24}$ substituted succinimide of Example 5 is diluted with 400 parts xylene. The temperature is held at 140° C. for 5 hours and the volatiles are removed by vacuum distillation to 15 mm Hg. The reaction mixture is filtered through a filter aid material to give the desired product.

EXAMPLE 19

Charged to a reactor are 463 parts (4.72 equivalents) of maleic anhydride and 1000 parts (5.95 equivalents) of polypropylene tetramer. This reaction mixture is heated to 182° C. held at this temperature for 9 hours. Unreacted starting materials are removed by vacuum distillation at 190° C. and 10mm Hg. The reaction mixture is filtered to yield the desired polypropylene tetramersubstituted succinic anhydride having an acid number to phenolphthalein of 428.

EXAMPLE 20

A reaction vessel containing 2368 parts (8 moles) of the polypropylene tetramer substituted succinic anhydride of Example 19 is heated to 120° C. Gaseous ammonia, 136 parts (8 moles), is slowly bubbled below the surface over 7.5 hours during which the temperature of the reaction mixture is increased to 155° C. Water of reaction is removed continuously during the $NH_3$ addition. The reaction mixture is filtered through a filter aid material to yield the polypropylene tetramer substituted succinimide having a 5.18% nitrogen content and an acid number to phenolphthalein of 44.

EXAMPLE 21

A mixture of 442.5 parts (1.5 moles) of the polypropylene tetramer substituted succinimide of Example 20, 84 parts of (1.5 moles) potassium hydroxide and 250 parts toluene are heated to reflux for 2 hours and water is removed by azeotropic distillation. This reaction mixture is cooled to 90° C. and 102 parts (0.75 moles) of zinc chloride is added and the temperature is increased to reflux and held for 7 hours. Diluent oil, 186 parts, is added at 90° C. and the volatiles are removed by stripping at 120° C. under 30-40 mm Hg vacuum. The reaction mixture is filtered through a filter aid material to give the desired product having a 3.2% nitrogen content and 7.49% zinc content.

EXAMPLE 22

A mixture of 135 parts (0.3 moles) of the $C_{18-24}$ succinimide of Example 5 and 16.8 parts (0.3 moles) of potassium hydroxide pellets are heated to reflux and water is removed by distillation. 100 parts toluene is charged to give the desired product containing 40% toluene.

EXAMPLE 23

A mixture of 252 parts (0.3 moles) of the product of Example 22, 200 parts toluene and 30 parts (0.15 moles) copper acetate monohydrate are heated to reflux while nitrogen is blown through the reaction mixture at 0.5 cubic feet per hour to remove water by azeotropic distillation. The reaction mixture is filtered through a filter aid material. Diluent oil, 261 parts, is added to the filtrate and the filtrate is stripped to 120° C. at 15 mm Hg to give the desired product having 0.9% nitrogen, 1.96% copper content, a base number to bromophenol blue of 37.9 and an acid number to phenolphthalein of 12.8.

EXAMPLE 24

A mixture of 620 parts (1.5 moles) of the $C_{18-24}$ substituted succinimide of Example 5, 500 parts xylene, and 675 parts duluent oil is heated to 80° C. and 50 parts water and 55.5 parts (0.75 moles) calcium hydroxide are added. The reaction mixture is stripped to 180° C. under 12 mm Hg vacuum. The reaction mixture is filtered through a filter aid material to yield the desired product having a 1.96% calcium content and a 1.55% nitrogen content.

As previously indicated, the compositions of this invention are also useful as additives for lubricants, in which they can function primarily as friction modifiers and/or deposit softeners. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-polyisopropylene glycol ether having an average molecular weight of 1000, diphenyl ether of poly-ethylene glycol having a molecular weight of 500-1000, diethyl ether of polypropylene glycol having a molecular weight of 1000-1500); and mono- and polycarboxylic esters thereof, for example, the acetic acid esters, mixed $C_3$-$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol, etc.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain an amount of the composition of this invention sufficient to provide it with friction modification and/or deposit softening properties. Normally, this amount employed will be about 0.05 percent to about 20 percent, preferably about 0.1 percent to about 10 percent of the total weight of the lubricating composition. This amount is exclusive of solvent/diluent medium. In lubricating compositions operated under extremely adverse conditions, such as lubricating compositions for marine diesel engines, the compositions of this invention may be present in amounts of up to about 30 percent by weight, or more, of the total weight of the lubricating composition.

The term "minor amount" as used in the specification and appended claims is intended to mean that when a composition contains a "minor amount" of a specific material that amount is less than 50 percent by weight of the composition.

The term "major amount" as used in the specification and appended claims is intended to mean that when a composition contains a "major amount" of a specific material that amount is more than 50 percent by weight of the composition.

The invention also contemplates the use of other additives in combination with the compositions of this invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature of at least about 50° C. and filtering the resulting mass. The use of a "promoter" in the neutralization step to aid the incorporation of a large excess of metal likewise is known. Examples of compound useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a nonvolatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Patent 1,306,529 and in many U.S. patents including the following:

| | | |
|---|---|---|
| 3,163,603 | 3,351,552 | 3,541,012 |
| 3,184,474 | 3,381,022 | 3,543,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,197 | |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

| | | |
|---|---|---|
| 2,459,112 | 3,442,808 | 3,591,598 |
| 2,962,442 | 3,448,047 | 3,600,372 |
| 2,984,550 | 3,454,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-subsituted acrylates. These may be characterized as "polymeric dispersants" and examples thereof are disclosed in the following U.S. Pat. Nos.

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)-disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl napthyl phosphite, oleyl 4-pentylphenyl phosphite, polypropylene (molecular weight 500 )-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di (heptylphenyl) -phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 10 percent to 90 percent by weight of the composition of this invention and may contain, in addition, one or more other additives known in the art or described hereinabove.

The fuel compositions of the present invention contain a major proportion of a normally liquid fuel, usually a hydrocarbonaceous petroleum distillate fuel such as motor gasoline as defined by ASTM Specification D-439-73 and diesel fuel or fuel oil as defined by ASTM Specification D-396. Normally liquid fuel compositons comprising nonhydrocarbonaceious materials such as alcohols, ethers, organonitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid-fuels which are mixtures of one or more hydrocarbonaceous fuels and one or more nonhydrocarbonaceous materials are also contemplated. Examples of such mixtures are combinations of gasoline and ethanol, and diesel fuel and ether. Particularly preferred is gasoline, that is, a mixture of hydrocarbons having an ASTM boiling point of about 60° C. at the 10 percent distillation point to about 205° C. at the 90 percent distillation point.

Generally, these fuel compositions contain an amount of the composition of this invention sufficient to impart friction modification and/or deposit softening properties to the fuel; usually this amount is bout 0.001 to about 5 percent (based on the weight of the final composition), preferably 0.001 percent to 1.0 percent.

The fuel compositions of this invention can contain, in addition to the compositions of this invention, other additives which are well known to those of skill in the art. These can include antiknock agents such as tetraalkyl lead compounds, lead scavengers such as haloalkanes (e.g., ethylene dichloride and ethylene dibromide), deposit preventors or modifiers such as triaryl phosphates, dyes, cetane improvers, auxiliary antioxidants such as 2,6-ditertiary-butyl-4-methylphenol, rust inhibitors such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the aforedescribed compositions are combined with an ashless dispersant in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Patent No. 1,396,645, British Patent Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British Patent Specification 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0, preferably about 1 to about 10 parts of composition to 1 part ashless dispersant. In still another embodiment of this invention, the inventive additives are combined with Mannich condensation products formed from substituted phenols, aldehydes, polyamines, and substituted pyridines. Such condensation products are described in U.S. Pat. Nos. 3,649,659; 3,558,743; 3,539,633; 3,704,308; and 3,725,277.

The compositions of this invention can be added directly to the fuel to form the fuel compositions of this invention or they can be diluted with a substantially inert, normally liquid organic solvent/diluent such as mineral oil, xylene, or a normally liquid fuel as described above, to form an additive concentrate which is then added to the fuel in sufficient amounts to form the inventive fuel composition described herein. These concentrates generally contain about 10 to 90 percent of the compositions of this invention and can contain in addition any of the abovedescribed conventional additives, particularly the aforedescribed ashless dispersants in the aforesaid proportions. The remainder of the concentrate is the solvent/diluent.

The lubricant fuel and additive concentrate compositions of this invention are exemplified by the following Table. All amounts other than those for mineral oil are exclusive of oil used as diluent.

| COMPONENT | I | II | III | IV | V | VI | VII | VIII | IX | X | XI | XII | XIII |
|---|---|---|---|---|---|---|---|---|---|---|---|---|---|
| Mineral Oil | 92.87 | 92.87 | 92.87 | 92.87 | 92.87 | 92.87 | 92.85 | 86.466 | 86.466 | 86.466 | 86.40 | 86.75 | 86.10 |
| Reaction Product of Malan-Styrene Copolymer with alcohol and heterocyclic amine | | | | | | | | .124 | .124 | .124 | .12 | .12 | .123 |
| Hydrogenated styrene-isoprene non-dispersant viscosity improver | | | | | | | | 8.93 | 8.93 | 8.93 | 8.87 | 8.91 | 8.84 |
| Polybutenyl succinic anhydride ethylene polyamine reaction product | 1.94 | 1.94 | 1.94 | 1.94 | 1.94 | 1.94 | 1.97 | 1.71 | 1.71 | 1.71 | 1.71 | 1.71 | 1.70 |
| Styrene-alkyl maleate copolymer | 1.79 | 1.79 | 1.79 | 1.79 | 1.79 | 1.79 | 1.75 | | | | | | |
| Zinc isooctylphosphrodithioate | .78 | .78 | .78 | .78 | .78 | .78 | .81 | | | | | | |
| Zinc methylamylphosphoridithioate | .67 | .67 | .67 | .67 | .67 | .67 | .684 | | | | | | |
| Zinc salt of mixed isobutyl and primary amyl phosphorodithioates | | | | | | | | .48 | .48 | .48 | .48 | .48 | .48 |
| Zinc salt of mixed isopropyl and primary amyl phosphorodithioates | | | | | | | | .55 | .55 | .55 | .55 | .55 | .54 |
| Basic calcium petroleum sulfonate | .52 | .52 | .52 | .52 | .52 | .52 | .522 | .25 | .25 | .25 | .25 | .25 | .25 |
| Basic sodium petroleum sulfonate | .42 | .42 | .42 | .42 | .42 | .42 | .41 | .30 | .30 | .30 | .30 | .30 | .30 |
| Basic magnesium petroleum sulfonate | | | | | | | | .29 | .29 | .29 | .28 | .28 | .28 |
| Sulfurized Diels-Alder Adduct | | | | | | | | .20 | .20 | .20 | .19 | .20 | .20 |
| Alkylated Aryl Amines | | | | | | | | .09 | .09 | .09 | .09 | .09 | .09 |
| Oleamide/linoleamide mixture | | | | | | | | .104 | .104 | .104 | .10 | .104 | .10 |
| Silicon antifoamant | .005 | .005 | .005 | .005 | .005 | .005 | .005 | .006 | .006 | .006 | .006 | .006 | .006 |
| Product of Example 5 | 1.000 | | | | | | | .50 | | | | | |
| Product of Example 7 | | 1.000 | | | | | | | .50 | | | | |
| Product of Example 14 | | | 1.000 | | | | | | | | | | |
| Product of Example 15 | | | | 1.000 | | | | | | | .50 | | |
| Product of Example 2 | | | | | 1.000 | | | | | | | | |
| Product of | | | | | | 1.000 | 1.000 | | | | | | |

-continued

| COMPONENT | I | II | III | IV | V | VI | VII | VIII | IX | X | XI | XII | XIII |
|---|---|---|---|---|---|---|---|---|---|---|---|---|---|
| Example 6 Product of Example 11 | | | | | | | | | | | | | 1.000 |
| Product of Example 12 | | | | | | | | | | | .65 | .25 | |

The fuel consumption of engines lubricated with compositions of this invention is measurably lower than that of engines lubricated with previously known lubricants. This can be shown by the Motored Engine Friction Horsepower Test, in which an engine is driven by a dynamometer at constant temperature as engine rpm. and torque are measured by a digital tachometer and a precision dial manometer, respectively. Friction horsepower, as calculated from these values, is roughly proportional to fuel consumed and thus decreases with improved fuel economy.

What is claimed is:

1. A composition comprising one or more substituted succinimide derivatives represented by the formula:

$$\begin{array}{c} O \\ \| \\ R-CH-C \\ | \quad\quad\quad \diagdown \\ \quad\quad\quad\quad\quad N-X; \\ | \quad\quad\quad \diagup \\ CH_2-C \\ \| \\ O \end{array}$$

wherein X is $$-\underset{R_2}{\overset{R_1}{\underset{|}{\overset{|}{C}}}}-O-R_3, \quad (II)$$

wherein R is a hydrocarbon-based group containing from about 8 up to about 35 carbon atoms, $R_1$ and $R_2$ are each independently hydrogen or an alkyl group containing up to 8 carbon atoms wherein at least one of $R_1$ and $R_2$ is an alkyl group, $R_3$ is a hydrocarbon-based group containing up to about 28 carbon atoms.

2. A composition according to claim 1 wherein R is an aliphatic hydrocarbon group, free from acetylenic unsaturation, containing from about 10 up to about 30 carbon atoms, in which at least 8 carbon atoms are in a straight-chain configuration and one of $R_1$ and $R_2$ is hydrogen.

3. A composition according to claim 2 wherein $R_3$ is an aliphatic hydrocarbon group containing up to about 14 carbon atoms.

4. A composition prepared by reacting in the presence of a catalytic amount of base;
A) one or more substituted succinimides represented by the formula:

$$\begin{array}{c} O \\ \| \\ R-CH-C \\ | \quad\quad\quad \diagdown \\ \quad\quad\quad\quad\quad N-H; \\ | \quad\quad\quad \diagup \\ CH_2-C \\ \| \\ O \end{array}$$

wherein R is a hydrocarbon-based group containing from about 8 up to about 35 carbon atoms;

B) one or more carbonyl compounds represented by the formula:

$$\begin{array}{c} O \\ \| \\ R_1-C-R_2 \end{array}$$

wherein $R_1$ and $R_2$ are each independently hydrogen or an alkyl radical containing up to 8 carbon atoms;

C) one or more alcohols represented by the formula:

$$R_3-OH$$

wherein $R_3$ is a hydrocarbon-based group containing up to about 28 carbon-atoms.

5. A compositions according to claim 4 wherein at least one of $R_1$ and $R_2$ is hydrogen and $R_3$ is an alkyl radical containing up to about 14 carbon atoms.

6. A composition according to claim 5 wherein $R_1$ and $R_2$ are hydrogen, and about one mole of water for each mole of carbonyl compounds is removed from the reaction and wherein the molar ratio of reactants A:B:C is 1:1–1.3:1.

7. A process which comprises reacting in the presence of a catalytic amount of base:
A) one or more substituted succinimides represented by the formula:

$$\begin{array}{c} O \\ \| \\ R-CH-C \\ | \quad\quad\quad \diagdown \\ \quad\quad\quad\quad\quad N-H; \\ | \quad\quad\quad \diagup \\ CH_2-C \\ \| \\ O \end{array}$$

wherein R is hydrocarbon-based group containing from about 8 up to about 35 carbon atoms;

B) one or more carbonyl compounds represented by the formula:

$$\begin{array}{c} O \\ \| \\ R_1-C-R_2 \end{array}$$

wherein $R_1$ and $R_2$ are each independently hydrogen or an alkyl radical containing up to 8 carbon atoms; and C) one or more alcohols represented by the formula:

$$R_3-OH$$

wherein $R_3$ is a hydrocarbon-based group containing up to about 28 carbon atoms.

8. A process according to claim 7 wherein at least one of $R_1$ and $R_2$ hydrogen and $R_3$ is an alkyl radical containing up to about 14 carbon atoms.

9. A process according to claim 8 wherein $R_1$ and $R_2$ are hydrogen, and about one mole of water for each mole of carbonyl compound is removed from the reaction and wherein the molar ratio of reactants A:B:C is 1:1–1.3:1.

10. An additive concentrate comprising a substantially inert, normally liquid organic diluent and from about 10 percent up to about 90 percent by weight of a composition according to claim 1.

11. A lubricating composition comprising a major amount of a lubricating oil and a minor amount of at least one composition according to claim 1.

12. A method for reducing fuel composition in an internal combustion engine which comprises lubricating said engine during operation with at least one lubricating composition according to claim 11.

* * * * *